United States Patent [19]

Schurter et al.

[11] Patent Number: 4,932,997
[45] Date of Patent: Jun. 12, 1990

[54] N-HETEROCYCLOSULFONYL-N'-AND N-HETEROCYCLOSULFONYL-N'-TRIAZINYLUREAS

[75] Inventors: Rolf Schurter, Binningen; Willy Meyer, Riehen; Werner Föry, Basel, all of Switzerland

[73] Assignee: Ciba-Geigy Corporation, Ardsley, N.Y.

[21] Appl. No.: 719,614

[22] Filed: Apr. 3, 1985

[30] Foreign Application Priority Data

Apr. 11, 1984 [CH] Switzerland ............ 1822/84

[51] Int. Cl.$^5$ .................. C07D 409/12; A01N 43/66; A01N 43/54
[52] U.S. Cl. .................................. 71/90; 71/92; 71/93; 544/320; 544/321; 544/324; 544/327; 544/331; 544/198; 544/207; 544/209; 544/212
[58] Field of Search ............... 71/92, 90, 93; 544/320, 544/321, 324, 327, 331, 212, 207, 209, 198

[56] References Cited

U.S. PATENT DOCUMENTS 4,473,394 9/1984 Budzinski et al. ............ 544/212
4,496,392 1/1985 Levitt ........................... 544/321
4,668,279 5/1987 Rorer ........................... 544/331
4,684,393 8/1987 Shapiro ........................ 71/90

FOREIGN PATENT DOCUMENTS 103543 3/1984 European Pat. Off. ........ 544/212

Primary Examiner—John M. Ford
Attorney, Agent, or Firm—Kevin T. Mansfield

[57] ABSTRACT

N-Heterocyclosulfonyl-N'-pyrimidinylureas and N-heterocyclosulfonyl-N'-triazinylureas of the formula

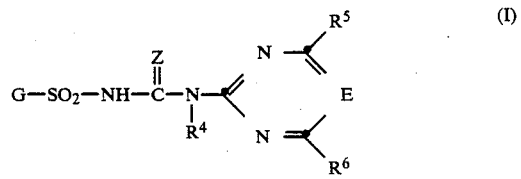

wherein
E is nitrogen or the methine bridge,
Z is oxygen or sulfur,
$R^4$ is hydrogen or $C_1$–$C_4$alkyl,
$R^5$ and $R^6$ are each independently hydrogen, halogen, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_3$–$C_6$dialkoxyalkyl, $C_1$–$C_4$haloalkylthio, $C_2$–$C_4$-alkoxyalkyl, $C_3$–$C_6$cycloalkyl or —$NR^{12}R^{13}$,
G is a

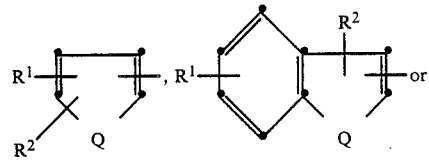

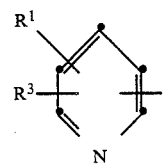

group $R^1$ is hydrogen, halogen, nitro, $C_1$–$C_4$alkyl, $C_1$–$C_4$alkoxy, trifluoromethyl, trifluoromethoxy, difluoromethoxy, $C_1$–$C_4$alkyl carbonyl or —$COOR^{14}$,
$R^2$ is a

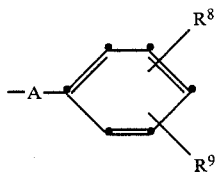

group,
$R^3$ is a

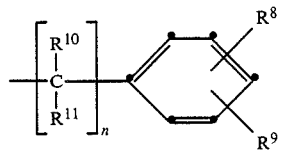

Q is oxygen, sulfur or —$NR^7$—,
A is oxygen, sulfur, —SO—, —$SO_2$— or —$(CR^{10}R^{11})_m$—,
m and n are 0, 1 or 2,
$R^7$ is hydrogen, $C_1$–$C_4$alkyl, $C_3$–$C_6$cycloalkyl, benzyl oder phenyl,
$R^8$ is hydrogen, $C_1$–$C_4$alkyl, $C_1$–$C_4$alkoxy, halogen, $C_1$–$C_4$haloalkyl, nitro, —$COOR^{14}$, $C_1$–$C_4$haloalkoxy, —O—$CR^{15}R^{16}$—$COOR^{14}$ or —O—$CR^{15}R^{16}$—CN,
$R^9$ is hydrogen, halogen, $C_1$–$C_4$alkyl, $C_1$–$C_4$alkoxy, $C_2$–$C_4$alkoxyalkyl oder $C_2$–$C_4$alkoxyalkoxy,
$R^{10}$ and $R^{11}$ are each independently hydrogen or $C_1$–$C_4$alkyl,
$R^{12}$ and $R^{13}$ are each independently hydrogen or $C_1$–$C_4$alkyl,
$R^{14}$ is hydrogen, $C_1$–$C_4$alkyl, $C_2$–$C_4$alkenyl, $C_3$–$C_4$alkynyl, or is $C_1$–$C_4$alkyl which is substituted by $C_1$–$C_4$alkoxy, halogen or phenyl, and
$R^{15}$ and $R^{16}$ are each independently hydrogen or $C_1$–$C_4$alkyl, and the salts thereof have useful selective herbicidal properties for controlling weeds in crops of useful plants.

17 Claims, No Drawings

N-HETEROCYCLOSULFONYL-N'-PYRIMIDINYLUREAS AND N-HETEROCYCLOSULFONYL-N'-TRIAZINYLUREAS

The present invention relates to novel sulfonylureas with herbicidal and plant growth regulating properties, to the preparation thereof, to compositions containing them as active ingredients, and to methods of using them for controlling weeds, preferably selectively, in crops of useful plants, or for regulating and inhibiting plant growth. The invention further relates to novel sulfonamides prepared as intermediates and to derivatives thereof.

The invention relates to sulfonylureas of the formula I

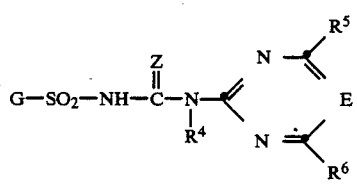

wherein
E is nitrogen or the methine bridge,
Z is oxygen or sulfur,
$R^4$ is hydrogen or $C_1$-$C_4$alkyl,
$R^5$ and $R^6$ are each independently hydrogen, halogen, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_3$-$C_6$dialkoxyalkyl, $C_1$-$C_4$haloalkylthio, $C_2$-$C_4$-alkoxyalkyl, $C_3$-$C_6$cycloalkyl or —$NR^{12}R^{13}$,
G is a

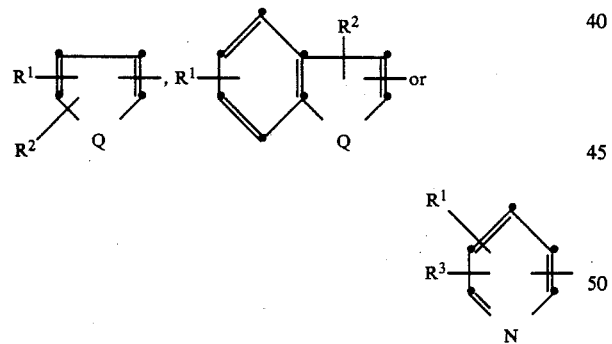

group $R^1$ is hydrogen, halogen, nitro, $C_1$-$C_4$alkyl, $C_1$-$C_4$alkoxy, trifluoromethyl, trifluoromethoxy, difluoromethoxy, $C_1$-$C_4$alkylcarbonyl or —$COOR^{14}$,
$R^2$ is a

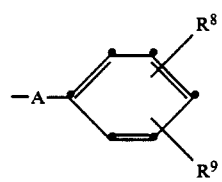

group,
$R^3$ is a

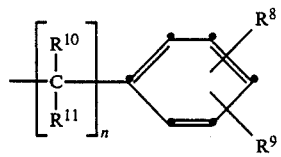

group,
Q is oxygen, sulfur or —$NR^7$—,
A is oxygen, sulfur, —SO—, —$SO_2$— or —$(CR^{10}R^{11})_m$—,
m and n are 0, 1 or 2,
$R^7$ is hydrogen, $C_1$-$C_4$alkyl, $C_3$-$C_6$cycloalkyl, benzyl oder phenyl,
$R^8$ is hydrogen, $C_1$-$C_4$alkyl, $C_1$-$C_4$alkoxy, halogen, $C_1$-$C_4$haloalkyl, nitro, —$COOR^{14}$, $C_1$-$C_4$haloalkoxy, —O—$CR^{15}R^{16}$—$COOR^{14}$ or —O—$CR^{15}R^{16}$—CN,
$R^9$ is hydrogen, halogen, $C_1$-$C_4$alkyl, $C_1$-$C_4$alkoxy, $C_2$-$C_4$alkoxyalkyl oder $C_2$-$C_4$alkoxyalkoxy,
$R^{10}$ and $R^{11}$ are each independently hydrogen or $C_1$-$C_4$alkyl,
$R^{12}$ and $R^{13}$ are each independently hydrogen or $C_1$-$C_4$alkyl,
$R^{14}$ is hydrogen, $C_1$-$C_4$alkyl, $C_2$-$C_4$alkenyl, $C_3$-$C_4$alkynyl, or is $C_1$-$C_4$alkyl which is substituted by $C_1$-$C_4$alkoxy, halogen or phenyl, and
$R^{15}$ and $R^{16}$ are each independently hydrogen or $C_1$-$C_4$alkyl,
and to the salts thereof.

Ureas, triazines and pyrimidines with herbicidal properties are generally known in the art. Sulfonylureas with herbicidal and plant growth regulating action have recently been described, for example in published European patent applications 39 239, 41 404, 45 196, 57 456, 64 804 and 70 698.

In the above definitions, alkyl denotes straight chain or branched alkyl, e.g. methyl, ethyl, n-propyl, isopropyl, or the four butyl isomers.

Alkoxy denotes methoxy, ethoxy, n-propyloxy, isopropyloxy, or the four butyloxy isomers, with methoxy, ethoxy or isopropyloxy being preferred.

Alkylthio is e.g. methylthio, ethylthio, n-propylthio, isopropylthio, or the four butylthio isomers, with methylthio and ethylthio being preferred.

Cycloalkyl is generally cyclopropyl, cyclobutyl, cyclopentyl or cyclohexyl.

Halogen itself or as moiety of a substituent such as haloalkoxy, haloalkylthio or haloalkyl is fluorine, chlorine and bromine, with fluorine and chlorine being preferred. Haloalkyl itself or as moiety of haloalkoxy or haloalkylthio is normally chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, 1,1,2,3,3,3-hexafluoropropyl, with fluoromethyl, chloromethyl, difluoromethyl and trifluoromethyl being preferred.

Alkoxyalkyl is e.g. methoxymethyl, methoxyethyl, methoxypropyl, ethoxyethyl, ethoxymethyl or propyloxymethyl. Alkoxyalkoxy is e.g. methoxymethoxy, methoxyethoxy, methoxypropyloxy, ethoxymethoxy, ethoxyethoxy and propyloxymethoxy. Within the scope of the present invention, dialkoxyalkyl will generally be understood as meaning the following radicals: dimethoxymethyl, 2,2-dimethoxyethyl, 1,2-dimethoxyethyl, 1,2-diethoxyethyl, 2,2-diethoxyethyl, 2,2-dimethoxypropyl, 3,3-dimethoxypropyl, 1,1-dimethoxyethyl, 1,1-diethoxyethyl, 1,1-dimethoxypropyl, 2,3-dimethoxypropyl, 1,1-dimethoxybutyl, 2,2-dimethoxybutyl, 3,3-dimethoxybutyl, 4,4-dimethoxybutyl, with the geminal dialkoxyalkyl radicals, which may also be designed as acetals, being preferred.

Alkenyl radicals are vinyl, allyl, 2-butenyl, 3-butenyl or methallyl. Alkynyl is propargyl, 2-butynyl or 3-butynyl. Allyl and propargyl are preferred.

Alkylcarbonyl radicals are in particular acetyl, propionyl, butyryl, isobutyryl, valeryl, isovaleryl or pivaloyl.

The aromatic heterocyclene systems as defined for G comprise e.g. the following basic heterocycles: pyridine, pyrrole, furan, thiophene, benzo[b]thiophene, benzo[b]furan or indole.

The invention also comprises the salts which the compounds of formula I are able to form with amines, alkali metal bases and alkaline earth metal bases, or with quaternary ammonium bases.

Preferred salt-forming alkali metal hydroxides and alkaline earth metal hydroxides are the hydroxides of lithium, sodium, potassium, magnesium or calcium, most preferably those of sodium or potassium.

Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine, diethanolamine and 1,4-diazabicyclo[2.2.2]octane being most preferred.

Examples of quaternary ammonium bases are, in general, the cations of haloammonium salts, e.g. the tetramethylammonium cation, the tetraethylammonium cation, the trimethylethylammonium cation, and also the ammonium cation.

Among the compounds of formula I, those compounds are preferred wherein either
(a) Z is oxygen or
(b) $R^1$ is hydrogen, Cl, F, $CH_3$, $C_2H_5$, $CH_3O$, $CF_3$, $CH_3CO$ or
(c) $R^5$ and $R^6$ together contain not more than 4 carbon atoms and $R^4$ is hydrogen or
(d) G is 3-phenylpyridin-2-yl or
(e) G is 2-phenylbenzo[b]thiophen-3-yl or 2-phenoxybenzo[b]thiophen-3-yl or
(f) G is 3-phenylthiophen-2-yl, 3-phenoxythiophen-3-yl or 2-phenylthiophen-3-yl, each unsubstituted or substituted by Cl, $CH_3$ or $CH_3O$, or
(g) G is 3-phenylfuran-2-yl oder 2-phenylfuran-3-yl or
(h) G is 2-$C_1$-$C_4$alkoxycarbonyl-4-phenylthiophen-3-yl oder 2-$C_1$-$C_4$-alkoxycarbonyl-5-phenylthiophen-3-yl.

A further preferred subgroup of compounds of formula I comprises those compounds wherein either (aa) Z is oxygen, $R^4$ is hydrogen and G is 3-phenylpyridin-2-yl and $R_5$ and $R_6$ together contain not more than 4 carbon atoms or
(bb) Z is oxygen, $R^4$ is hydrogen and G is 2-phenylbenzo[b]thiophen-3-yl or 2-phenoxybenzo[b]thiophen-3-yl or $R^5$ and $R^6$ together contain not more than 4 carbon atoms or
(cc) Z is oxygen, $R^4$ is hydrogen and G is 3-phenylthiophen-2-yl, 3-phenoxythiophen-2-yl, 2-phenylthiophen-3-yl, 3-phenylfuran-2-yl or 2-phenylfuran-3-yl and $R^5$ and $R^6$ together contain not more than 4 carbon atoms or
(dd) Z is oxygen, $R^4$ is hydrogen and G is 2-$C_1$-$C_4$alkoxycarbonyl-4-phenylthiophen-3-yl or 2-$C_1$-$C_4$alkoxycarbonyl-5-phenylthiophen-3-yl and $R^5$ and $R^6$ together contain not more than 4 carbon atoms.

Preferred individual compounds of formula I are:
N-(2-phenylbenzo[b]thiophen-3-ylsulfonyl)-N'-(4-methoxy-6-methylpyrimidin-2-yl)urea and
N-(2-methoxycarbonyl-4-phenylthiophen-3-ylsulfonyl)-N'-(4-methoxy-6-methylpyrimidin-2-yl)urea.

The preparation of the compounds of formula I is generally carried out by the following methods.

In accordance with a first process, the compounds of formula I are obtained by reacting a substituted sulfonamide of formula II

$$G-SO_2-NH_2 \qquad (II)$$

wherein G is as defined for formula I, with a carbamate of formula III

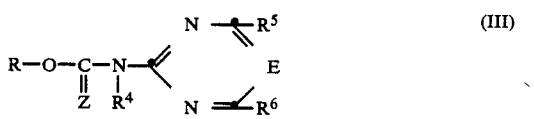

wherein E, $R^4$, $R^5$, $R^6$ and Z are as defined for formula I and R is phenyl, alkyl or substituted phenyl, in the presence of a base.

In accordance with a second process, the compounds of formula I are obtained by reacting a sulfonylcarbamate of formula IV

wherein G and Z are as defined for formula I and R is phenyl, alkyl or substituted phenyl, with an amine of formula V

wherein E, $R^4$, $R^5$ and $R^6$ are as defined for formula I.

Finally, the compounds of formula I can also be obtained by reacting a sulfonylisocyanate of formula VI

$$G-SO_2-N=C=Z \qquad (VI)$$

wherein G and Z are as defined for formula I, with an amine of formula V above.

If desired, the resultant ureas of formula I can be converted into addition salts with amines, alkali metal hydroxides or alkaline earth metal hydroxides or with quaternary ammonium bases. This is accomplished e.g. by reaction with the equimolar amount of base and by evaporating off the solvent.

It is convenient to carry out these reactions for obtaining compounds of formula I in aprotic, inert organic solvents. Examples of suuch solvents are hydrocarbons such as benzene, toluene, xylene or cyclohexane, carbon tetrachloride, or chlorobenzene; ethers such as diethyl ether, ethylene glycol diemthyl ether, diethylene glycol dimethyl ether, tetrahydrofuran or dioxane; nitriles such as acetonitrile or propionitrile; amides such as dimethylformamide, diethylformamide or N-methylpyrrolidinone. The reaction temperatures are preferably in the range from $-20°$ C. to $+120°$ C. The coupling reactions are normally slightly exothermic and can be carried out at room temperature. To shorten the reaction time or also to initiate the reaction, it is expedient to heat the reaction mixture briefly to boiling point. The reaction times can also be shortened by addition of a few drops of a base as catalyst. Preferred bases are tertiary amines such as trimethylamine, triethylamine, quinuclidine, 1,4-diazabicyclo[2.2.2]octane, 1,5-diazabicyclo[4.3.0]non-5-ene or 1,8-diazabicyclo[5.4.-0]undec-7-ene. However, the bases employed may also be inorganic bases, e.g. hydrides such as sodium hydride or calcium hydride, hydroxides such as sodium hydroxide or potassium hydroxide, carbonates such as sodium carbonate or potassium carbonate, or bicarbonates such as potassium bicarbonate or sodium bicarbonate.

The final products of formula I can be isolated by concentrating and/or evaporating off the solvent and purified by recrystallising or triturating the solid residue in solvents in which they are not readily soluble, e.g. an ether, an aromatic hydrocarbon or a chlorinated hydrocarbon.

The intermediates of formulae II, IV and VI are novel. They have been specially developed for the synthesis of compounds of formula I and therefore constitute a further object of the present invention.

The intermediates of formula II are prepared by processes known per se. Thus, for example, the compounds of formula II are obtained by diazotising an amine of formula VII $$G-NH_2 \qquad (VII)$$

wherein G is as defined for formula I, in hydrochloric acid, and reacting the diazo group with sulfur dioxide in the presence of a catalyst such as copper chloride and reacting the resultant sulfonyl chloride of formula VIII $$G-SO_2-Cl \qquad (VIII)$$

wherein G is as defined for formula I, with ammonia. The corresponding starting amines are known or they can be obtained by known processes, e.g. by reduction from the corresponding nitro compounds.

Further, the compounds of formula II can be obtained by converting a sulfonic acid of formula IX $$G-SO_2-OH \qquad (IX)$$

wherein G is as defined for formula I, by treatment with a chlorinating agent such as $PCl_5$, $POCl_3$, $COCl_2$ or $SOCl_2$, to give the corresponding sulfonyl chloride of formula VIII and reacting said chloride with ammonia.

Likewise, the compounds of formula II can be obtained by treating a benzyl thioether of formula X $$G-S-CH_2-C_6H_5 \qquad (X)$$

wherein G is as defined for formula I, with chlorine and reacting the resultant sulfonyl chloride of formula VIII with ammonia.

In some cases the sulfonyl chlorides of formula VIII are obtained by direct sulfochlorination of the substituted compound of formula XI $$G-H \qquad (XI)$$

wherein G is as defined for formula I, with chlorosulfonic acid $ClSO_3H$.

The phenylsulfonylisocyanates of formula VI can be obtained e.g. by phosgenating the sulfonamides of formula II, in the presence of butyl isocyanate and in an inert solvent, at reflux temperature. Similar reactions are described in "Neuere Methoden der präparativen organischem Chemie", Band VI, 211-229, Verlag Chemie, Weinheim, 1970.

The isothiocyanates of formula VI are obtained by treating the sulfonamides of formula II with carbon disulfide and potassium hydroxide and subsequently phosgenating the dipotassium salt. Such processes are described in Arch. Pharm. 229, 174 (1966).

The phenylsulfonylcarbamates of formula IV are obtained by reacting the sulfonamides of formula II with a carbonate in the presence of a base. Similar processes are described in Japanese patent specification 61 169.

The starting aminopyrimidines and aminotriazines of formula V and corresponding carbamates of formula III are either known or they can be prepared by known methods from compounds disclosed in the literature.

The compounds of formulae VII, VIII, IX, X and XI are known or can be prepared by methods analogous to known ones.

The compounds of formula I are stable compounds and no precautionary measures are required for handling them.

When used at low rates of application, the compounds of formula I have good selective growth inhibiting and selective herbicidal properties which make them most suitable for use in crops of useful plants, preferably in cereals, cotton, soybeans and maize, and most preferably in rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of formula I are effective even when used at very low rates of application.

The compounds of formula I have in addition pronounced growth regulating, especially growth inhibiting, properties. The growth of both monocots and dicots is inhibited.

Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators resides in the fact that nutrients are able increasingly to promote flower formation and fruiting, whereas vegetative growth is inhibited.

At higher rates of application of compounds of formula I, all tested plants are so severely damaged in their development that they die.

The invention also relates to herbicidal and growth regulating compositions which contain a novel compound of formula I, and also to methods of controlling weeds pre- and postemergence and of inhibiting the growth of monocots and dicots, especially grasses, tropical cover crops and tobacco plant suckers.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of applications, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidized coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a napthalenesulfonic acid/formaldehyde condensation product.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. strearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981; M. and J. Ash, "Encyclopedia of Surfactants", Vol. I–III, Chemical Publishing Co., New York, 1980-81.

The herbicidal compositions usually contain 0.1 to 95%, preferably 0.1 to 80%, of a compound of formula I, 1 to 99.9%, of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 24%, preferably 88 to 30% |
| surfactant: | 1 to 40%, preferably 2 to 30% |
| Wettable powders | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001% of active ingredient. The rates of application are normally from 0.01 to 10 kg a.i./ha, preferably from 0.025 to 5 kg a.i./ha.

The compositions may also contain further ingredients such as stabilisers, antifoams, viscosity regulators, binders, tackifiers, as well as fertilisers and other compounds for obtaining special effects.

PREPARATORY EXAMPLES

Example P1:

N-(2-Phenylbenzo[b]thiophen-3-ylsulfonyl)-N'-(4-methoxy-6-methylpyrimidin-2-yl)urea (compound 5.03)

(a) 2-Phenylbenzo[b]thiophen-3-ylsulfonyl chloride 6.9 g (50 mmol) of a 50% solution of sodium nitrite are added dropwise at 0°–5° C. to a suspension of 11.3 g (50 mmol) of 3-amino-2-phenylbenzo[b]thiophene in 40 g of ice water and 20 ml (150 mmol) of 32% hydrochloric acid. After the mixture has been stirred at the same temperature for 15 minutes, it is filtered over silica. This filtrate, together with 13 g (50 mmol) of a 40% solution of sodium hydrogensulfite, is added dropwise at 10°–15° C. to a solution of 1.2 g (5 mmol) of copper sulfate in 13 g (50 mmol) of a 40% solution of sodium hydrogensulfite and in 50 ml of 32% hydrochloric acid. The reaction mixture is stirred for a further 1.5 hours at 20°–25° C. and then extracted with 3×50 ml of methylene chloride. The combined organic extracts contain the desired 2-phenylbenzo[b]thiophen-3-ylsulfonyl chloride and can be used in the following reaction step without further purification.

(b) 2-Phenylbenzo[b]thiophen-3-ylsulfonylamide

With efficient stirring, the solution of 2-phenylbenzo[b]thiophen-3-ylsulfonyl chloride obtained in (a) is added dropwise at 20°–25° C. to a solution of 30 ml of 40% ammonia in 30 ml of water. After continued stirring for 16 hours, the mixture is concentrated to half its original volume and extracted with 2×50 ml of ethyl acetate. The combined organic extracts are dried over sodium sulfate and concentrated by evaporation. The residue is chromatographed over silica gel eluted with a mixture of toluene and ethyl acetate (2:1), affording 6.8 g of 2-phenylbenzo[b]thiophen-3-ylsulfonamide with a melting point of 185°–186° C.

(c) A mixture of 1.1 g (3.8 mmol) of 2-phenylbenzo[b]thiophen-3-ylsulfonylamide, 1.0 g (3.8 mmol) of N-(4-methoxy-6-methylpyrimidin-2-yl)phenylcarbamate, 0.6 g (4 mmol) of 1.8-diazabicyclo[5.4.0]undec-7-ene and 15 ml of dioxane is stirred for 4 hours at 20°–25° C. The reaction mixture is then taken up in 100 ml of water, acidified to pH 3 by adding 2N hydrochloric acid dropwise and then extracted with 3×30 ml of ethyl acetate. The combined extracts are dried and concentrated by evaporation. The residue is crystallised from ether, affording 1.35 g (78% of theory) of N-(2-phenylbenzo[b]thiophen-3-ylsulfonyl)-N'-(4-methoxy-6-methylprimidin-2-yl)urea with a melting point of 199°–202° C.

Example P2:
N-(2-Methoxycarbonyl-4-phenylthiophen-3-yl-sulfonyl)-N'-(4,6-dimethoxypyrimidin-2-yl)urea (compound 4.14)

(a) 2-Methoxycarbonyl-4-phenylthiophen-3-ylsulfonyl chloride 10.9 g (0.04 mol) of 3-amino-2-methoxycarbonyl-4-phenylthiophene are dissolved in 20 ml of concentrated hydrochloric acid and then diazotised at −5° C. with 3.65 g of sodium nitrite in 10 ml of water. 30 minutes after the dropwise addition of sodium nitrite, the solution of the diazonium salt is added in portions to a mixture of 20 ml of dichloroethane, 0.45 g of benzyltriethylammonium chloride, 0.3 g of copper(I) chloride, 0.3 g of copper(II) chloride and 6 g of sulfur dioxide. When the addition at 5°–10° C. of the solution of the diazonium salt is complete, the reaction mixture is stirred for 1 hour at room temperature and then extracted three times with dichloroethane. The combined extracts are treated with activated carbon, filtered and concentrated. The resultant 2-methoxycarbonyl-4-phenylthiophen-3-ylsulfonyl chloride can be used further in the following reaction step without purification.

(b) 2-Methoxycarbonyl-4-phenylthiophen-3-ylsulfonamide

The 2-methoxycarbonyl-4-phenylthiophen-3-ylsulfonyl chloride obtained in (a) is dissolved in 120 ml of tetrahydrofuran. Then at −10° C., 2.2 g of ammonia gas are introduced into the solution. Subsequently, the reaction mixture is stirred at room temperature. When the reaction is complete, the mixture is concentrated and the residue is then purified by chromatography over silica gel. The solvent (ethyl acetate/cyclohexane 2:1) is removed by distillation, affording 5.2 g of 2-methoxycarbonyl-4-phenylthiophen-3-ylsulfonamide with a melting point of 172°–175° C.

(c) 2.4 g (0.008 mol) of 2-methoxycarbonyl-4-phenylthiophen-3-ylsulfonamide, 2.2 g of N-(4,6-dimethoxypyrimidin-2-yl)phenylcarbamate, 1.2 g of 1,8-diazabicyclo[5.4.0]undec-7-ene and 30 ml of acetonitrile are stirred for 16 hours at room temperature. The reaction mixture is then poured into a mixture of ice and water and acidified with methanesulfonic acid. The resultant precipitate is filtered, washed with water and dried, affording 3.4 g (95%) of N-(2-methoxycarbonyl-4-phenylthiophen-3-ylsulfonyl)-N'-(4,6-dimethoxypyrimidin-2-yl)urea with a melting point of 225°–227° C.

The intermediates and final products listed in the following tables are prepared in analogous manner.

TABLE 1

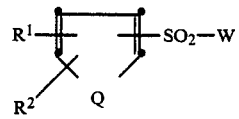

| Comp. | Q | W | Position —SO$_2$—W | R$^1$ | R$^2$ | m.p. [°C.] |
|---|---|---|---|---|---|---|
| 1.01 | O | NH$_2$ | 2 | H | 3-phenyl | |
| 1.02 | O | —NH—COOC$_6$H$_5$ | 2 | H | 3-phenyl | |
| 1.03 | S | NH$_2$ | 2 | H | 3-phenyl | |
| 1.04 | S | NH$_2$ | 2 | 5-CH$_3$ | 3-phenyl | |
| 1.05 | S | NH$_2$ | 2 | 5-Cl | 3-phenyl | |
| 1.06 | O | NH$_2$ | 2 | 5-CH$_3$—CO— | 3-phenyl | |
| 1.07 | S | NH$_2$ | 3 | H | 2-phenyl | |
| 1.08 | S | NH$_2$ | 5 | H | 2-phenyl | |
| 1.09 | S | NH$_2$ | 3 | H | 2-benzyl | |
| 1.10 | O | NH$_2$ | 3 | H | 2-benzyl | |
| 1.11 | S | NH$_2$ | 3 | H | 2-phenoxy | |
| 1.12 | O | —N=C=O | 2 | H | 3-phenyl | |
| 1.13 | O | —N=C=O | 3 | H | 2-phenyl | |
| 1.14 | S | —N=C=O | 2 | H | 3-phenyl | |
| 1.15 | S | —N=C=O | 3 | H | 2-phenyl | |
| 1.16 | S | NH$_2$ | 3 | 5-CH$_3$ | 2-phenoxy | |
| 1.17 | S | Cl | 3 | 2-COOCH$_3$ | 4-phenyl | |
| 1.18 | S | Cl | 3 | 2-COOC$_2$H$_5$ | 4-phenyl | |
| 1.19 | S | NH$_2$ | 3 | 2-COOCH$_3$ | 4-phenyl | 172–175 |
| 1.20 | S | NH$_2$ | 3 | 2-COOC$_2$H$_5$ | 4-phenyl | |
| 1.21 | S | Cl | 3 | 2-COOCH$_3$ | 5-phenyl | |
| 1.22 | S | Cl | 3 | 2-COOC$_2$H$_5$ | 5-phenyl | |
| 1.23 | S | NH$_2$ | 3 | 2-COOCH$_3$ | 5-phenyl | 180 |
| 1.24 | S | NH$_2$ | 3 | 2-COOC$_2$H$_5$ | 5-phenyl | 167 |
| 1.25 | S | NH$_2$ | 3 | H | 4-phenyl | |
| 1.26 | S | Cl | 3 | H | 4-phenyl | |
| 1.27 | S | Cl | 3 | 2-COOCH$_3$ | 4-(fluorophenyl) | |
| 1.28 | S | NH$_2$ | 3 | 2-COOCH$_3$ | 4-(2-fluorophenyl) | |
| 1.29 | S | Cl | 3 | 2-COOC$_2$H$_5$ | 4-(2-fluorophenyl) | |
| 1.30 | S | NH$_2$ | 3 | 2-COOC$_2$H$_5$ | 4-(2-fluorophenyl) | |
| 1.31 | S | Cl | 3 | 2-COOCH$_3$ | 4-(3-fluorophenyl) | |
| 1.32 | S | NH$_2$ | 3 | 2-COOCH$_3$ | 4-(3-fluoro- | |

TABLE 1-continued

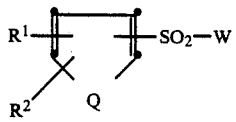

| Comp. | Q | W | Position —SO₂—W | R¹ | R² | m.p. [°C.] |
|---|---|---|---|---|---|---|
| | | | | | (phenyl) | |

TABLE 2

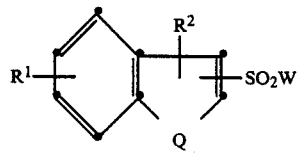

| Comp. | Q | W | Position —SO₂—W | R¹ | R² | m.p. [°C.] |
|---|---|---|---|---|---|---|
| 2.01 | S | NH₂ | 3 | H | 2-phenyl | 185–186 |
| 2.02 | O | NH₂ | 3 | H | 2-phenyl | |
| 2.03 | S | NH₂ | 3 | H | 2-phenoxy | |
| 2.04 | O | NH₂ | 3 | H | 2-phenoxy | |
| 2.05 | S | —NH—COOC₆H₅ | 3 | H | 2-phenyl | |
| 2.06 | S | —N=C=O | 3 | H | 2-phenyl | |
| 2.07 | S | Cl | 3 | H | 2-phenyl | oil |
| 2.08 | O | Cl | 3 | H | 2-phenyl | |

TABLE 3

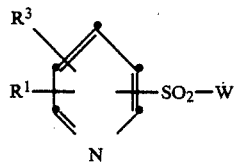

| Comp. | W | Position —SO₂—W | R¹ | R³ |
|---|---|---|---|---|
| 3.01 | NH₂ | 2 | H | 3-phenyl |
| 3.02 | NH₂ | 2 | H | 3-benzyl |
| 3.03 | NH₂ | 2 | 5-Cl | 3-phenyl |

TABLE 3-continued

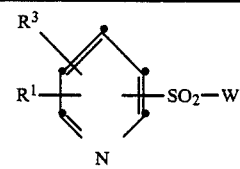

| Comp. | W | Position —SO₂—W | R¹ | R³ |
|---|---|---|---|---|
| 3.04 | NH₂ | 3 | 2-Cl | 6-phenyl |
| 3.05 | Cl | 3 | H | 3-phenyl |
| 3.06 | Cl | 3 | 5-Cl | 3-phenyl |

TABLE 4

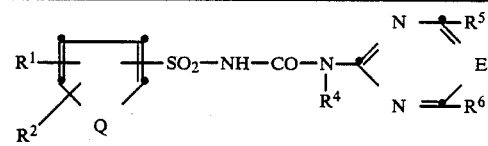

| Comp. | Q | Position —SO₂— | R¹ | R² | R⁴ | R⁵ | R⁶ | E | m.p. [°C.] |
|---|---|---|---|---|---|---|---|---|---|
| 4.01 | S | 2 | H | 3-phenyl | H | OCH₃ | OCH₃ | CH | |
| 4.02 | S | 2 | H | 3-phenyl | CH₃ | OCH₃ | CH₃ | CH | |
| 4.03 | O | 2 | H | 3-phenyl | H | OCH₃ | OCH₃ | CH | |
| 4.04 | O | 2 | H | 3-phenyl | H | OCH₃ | OCH₃ | N | |
| 4.05 | S | 2 | 5-CH₃ | 3-phenyl | H | OCH₃ | OCH₃ | CH | |
| 4.06 | S | 2 | 5-Cl | 3-phenyl | H | OCH₃ | OCH₃ | N | |
| 4.07 | O | 2 | 5-CH₃—CO— | 3-phenyl | H | OCH₃ | OCH₃ | CH | |
| 4.08 | S | 2 | H | 3-phenyl | H | OCH₃ | OCH₃ | N | |
| 4.09 | O | 3 | H | 2-phenyl | H | OCH₃ | OCH₃ | CH | |
| 4.10 | S | 3 | H | 2-phenyl | H | OCH₃ | OCH₃ | N | |
| 4.11 | S | 3 | H | 2-benzyl | H | OCH₃ | OCH₃ | CH | |
| 4.12 | O | 3 | H | 2-phenoxy | H | OCH₃ | OCH₃ | N | |
| 4.13 | S | 3 | H | 2-phenoxy | H | OCH₃ | OCH₃ | CH | |
| 4.14 | S | 3 | 2-COOCH₃ | 4-phenyl | H | OCH₃ | OCH₃ | CH | 225–227 |
| 4.15 | S | 3 | 2-COOCH₃ | 4-phenyl | H | OCH₃ | CH₃ | CH | 196 (decomp.) |
| 4.16 | S | 3 | 2-COOC₂H₅ | 5-phenyl | H | OCH₃ | OCH₃ | CH | 178–179 |

TABLE 4-continued $$R^1 \underset{R^2}{\overset{}{\diagdown}} Q \diagup - SO_2-NH-CO-\underset{R^4}{\overset{}{N}}\diagup \overset{N\overset{\bullet}{=\!=\!=}R^5}{\underset{N=\!=\!=R^6}{\diagdown}} E$$

| Comp. | Q | Position −SO$_2$− | R$^1$ | R$^2$ | R$^4$ | R$^5$ | R$^6$ | E | m.p. [°C] |
|---|---|---|---|---|---|---|---|---|---|
| 4.17 | S | 3 | 2-COOC$_2$H$_5$ | 5-phenyl | H | OCH$_3$ | CH$_3$ | CH | 202 (decomp.) |
| 4.18 | S | 3 | 2-COOCH$_3$ | 5-phenyl | H | OCH$_3$ | CH$_3$ | CH | 204–206 |
| 4.19 | S | 3 | 2-COOCH$_3$ | 5-phenyl | H | OCH$_3$ | OCH$_3$ | CH | 188–189 |
| 4.20 | S | 3 | H | 4-phenyl | H | OCH$_3$ | OCH$_3$ | CH | |
| 4.21 | S | 3 | H | 4-phenyl | H | CH$_3$ | OCH$_3$ | CH | |
| 4.22 | S | 3 | H | 4-phenyl | H | OCH$_3$ | OCH$_3$ | N | |
| 4.23 | S | 3 | H | 4-(2-fluorophenyl) | H | OCH$_3$ | CH$_3$ | CH | |
| 4.24 | S | 3 | H | 4-(2-fluorophenyl) | H | OCH$_3$ | OCH$_3$ | CH | |
| 4.25 | S | 3 | H | 4-(2-fluorophenyl) | H | OCH$_3$ | OCH$_3$ | N | |
| 4.26 | S | 3 | 2-COOCH$_3$ | 4-(2-fluorophenyl) | H | OCH$_3$ | OCH$_3$ | CH | |
| 4.27 | S | 3 | 2-COOCH$_3$ | 4-(2-fluorophenyl) | H | OCH$_3$ | OCH$_3$ | CH | |
| 4.28 | S | 3 | 2-COOC$_2$H$_5$ | 4-(2-fluorophenyl) | H | CH$_3$ | OCH$_3$ | CH | |
| 4.29 | S | 3 | 2-COOC$_2$H$_5$ | 4-(2-fluorophenyl) | H | OCH$_3$ | OCH$_3$ | CH | |
| 4.30 | S | 3 | 2-Cl | 4-(2-fluorophenyl) | H | OCH$_3$ | OCH$_3$ | CH | |
| 4.31 | S | 3 | 2-Cl | 4-(2-fluorophenyl) | H | CH$_3$ | OCH$_3$ | CH | |
| 4.32 | S | 3 | 2-Cl | 4-phenyl | H | CH$_3$ | OCH$_3$ | CH | |
| 4.33 | S | 3 | 2-Cl | 4-phenyl | H | OCH$_3$ | OCH$_3$ | CH | |
| 4.34 | S | 3 | 2-Cl | 4-phenyl | H | OCH$_3$ | OCH$_3$ | N | |
| 4.35 | S | 3 | 5-Cl | 4-phenyl | H | OCH$_3$ | OCH$_3$ | CH | |
| 4.36 | S | 3 | 5-Cl | 4-phenyl | H | CH$_3$ | OCH$_3$ | CH | |
| 4.37 | S | 3 | 2-COOCH$_3$ | 4-(4-methylphenyl) | H | CH$_3$ | OCH$_3$ | CH | |
| 4.38 | S | 3 | 2-COOCH$_3$ | 4-(4-methylphenyl) | H | OCH$_3$ | OCH$_3$ | CH | |
| 4.39 | S | 3 | 2-Cl | 5-phenyl | H | OCH$_3$ | OCH$_3$ | CH | |

TABLE 5

$$R^1 \underset{}{\diagdown} \overset{R^2}{\underset{Q}{\diagdown}} -SO_2-NH-CO-\underset{R^4}{\overset{}{N}}\diagup \overset{N\overset{\bullet}{=\!=\!=}R^5}{\underset{N=\!=\!=R^6}{\diagdown}} E$$

| Comp. | Q | Position −SO$_2$− | R$^1$ | R$^2$ | R$^4$ | R$^5$ | R$^6$ | E | m.p. [°C] |
|---|---|---|---|---|---|---|---|---|---|
| 5.01 | S | 3 | H | 2-phenyl | H | OCH$_3$ | OCH$_3$ | CH | 217–219 |
| 5.02 | S | 3 | H | 2-phenyl | H | OCH$_3$ | OCH$_3$ | N | |
| 5.03 | S | 3 | H | 2-phenyl | H | OCH$_3$ | CH$_3$ | CH | 199–202 |
| 5.04 | S | 3 | H | 2-phenyl | CH$_3$ | OCH$_3$ | CH$_3$ | CH | |
| 5.05 | O | 3 | H | 2-phenyl | H | OCH$_3$ | OCH$_3$ | CH | |
| 5.06 | S | 3 | H | 2-phenoxy | H | OCH$_3$ | OCH$_3$ | CH | |
| 5.07 | O | 3 | H | 2-phenoxy | H | OCH$_3$ | OCH$_3$ | CH | |
| 5.08 | S | 3 | H | 2-phenyl | H | OCH$_3$ | CH$_3$ | N | 187–188 |
| 5.09 | S | 3 | H | 2-phenyl | H | CH$_3$ | CH$_3$ | CH | |
| 5.10 | S | 3 | H | 2-(4-fluorophenyl) | H | OCH$_3$ | OCH$_3$ | CH | |

TABLE 5-continued

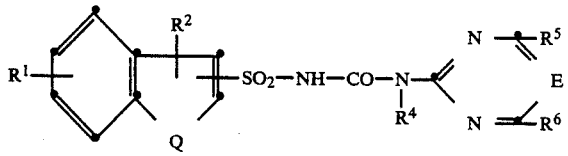

| Comp. | Q | Position —$SO_2$— | $R^1$ | $R^2$ | $R^4$ | $R^5$ | $R^6$ | E | m.p. [°C.] |
|---|---|---|---|---|---|---|---|---|---|
| 5.11 | S | 3 | H | 2-(4-fluoro-phenyl) | H | $OCH_3$ | $OCH_3$ | N | |
| 5.12 | S | 3 | H | 2-(4-fluoro-phenyl) | H | $OCH_3$ | $CH_3$ | CH | |
| 5.13 | S | 3 | H | 2-(4-fluoro-phenyl) | H | $OCH_3$ | $CH_3$ | N | |
| 5.14 | S | 3 | H | 2-(2-fluoro-phenyl) | H | $OCH_3$ | $OCH_3$ | CH | |
| 5.15 | S | 3 | H | 2-(2-fluoro-phenyl) | H | $OCH_3$ | $OCH_3$ | N | |
| 5.16 | S | 3 | H | 2-(2-fluoro-phenyl) | H | $OCH_3$ | $CH_3$ | CH | |
| 5.17 | S | 3 | H | 2-(2-fluoro-phenyl) | H | $OCH_3$ | $CH_3$ | N | |

TABLE 6

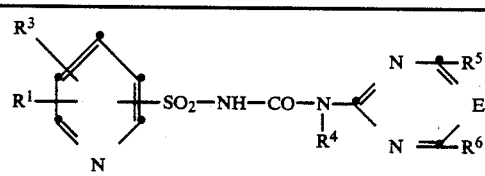

| Comp. | Position —$SO_2$— | $R^1$ | $R^2$ | $R^4$ | $R^5$ | $R^6$ | E |
|---|---|---|---|---|---|---|---|
| 6.01 | 2 | H | 3-phenyl | H | $OCH_3$ | $OCH_3$ | CH |
| 6.02 | 2 | H | 3-phenyl | H | $OCH_3$ | $OCH_3$ | N |
| 6.03 | 2 | H | 3-phenyl | $CH_3$ | $OCH_3$ | $OCH_3$ | CH |
| 6.04 | 2 | H | 3-benzyl | H | $OCH_3$ | $OCH_3$ | CH |
| 6.05 | 2 | 5-Cl | 3-phenyl | H | $OCH_3$ | $OCH_3$ | CH |
| 6.06 | 2 | 5-Cl | 3-phenyl | H | $OCH_3$ | $OCH_3$ | N |
| 6.07 | 3 | 2-Cl | 6-phenyl | H | $OCH_3$ | $OCH_3$ | CH |
| 6.08 | 3 | H | 3-phenyl | H | $CH_3$ | $OCH_3$ | CH |
| 6.09 | 3 | H | 3-phenyl | H | $CH_3$ | $OCH_3$ | N |

FORMULATION EXAMPLES

Example F1: Formulation Examples for compounds of formula I (percentages are by weight)

| (a) Wettable powders | (a) | (b) | (c) |
|---|---|---|---|
| compound of formula I | 20% | 50% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7-8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| compound of formula I | 10% | 1% |
| octylphenol polyethylene glycol ether (4-5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| compound of formula I | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| compound of formula I | 5% |
| isopropylamine | 1% |
| octylphenol polyethylene glycol ether (78 moles of ethylene oxide) | 3% |
| water | 91% |

BIOLOGICAL EXAMPLES

Example B1: Preemergence herbicidal action

Plastic pots are filled with expanded vermiculite (density: 0.135 g/cm$^3$, water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: *Nasturtium officinalis*, *Agrostis tenuis*, *Stellaria media* and *Digitaria sanguinalis*. The pots are then kept in a climatic chamber at 20° C., an illumination of about 20 klux and a relative humidity of 70%. During the germinating phase of 4 to 5 days, the pots are covered with lightpermeable material and watered with deionised water to increase the local humidity. After the 5th day, 0.5% of a commercial liquid fertiliser (Greenzit ®, ex Ciba-Geigy) is added to the water. The test is evaluated 12 days after sowing and the action on the plants is assessed according to the following rating:

1: plants have not emerged or are totally withered
2–3: very pronounced action
4–6: medium action
7–8: weak action
9: no action (as untreated controls).

Preemergence action

Concentration of the test compound emulsion: 70.8 ppm

| Test plant Compound | Nasturtium | Stellaria | Agrostis | Digitaria |
|---|---|---|---|---|
| 4.14 | 1 | 2 | 1 | 2 |
| 4.15 | 1 | 2 | 1 | 2 |
| 4.16 | 2 | 2 | 2 | 2 |
| 4.17 | 2 | 2 | 3 | 2 |
| 4.19 | 2 | 3 | 3 | 3 |
| 5.03 | 1 | 2 | 1 | 3 |

-continued

| Test plant Compound | Nasturtium | Stellaria | Agrostis | Digitaria |
|---|---|---|---|---|
| 5.08 | 2 | 2 | 1 | 2 |

Example B2: Growth inhibition of tropical leguminous cover crops

The test plants (*Centrosema plumieri* and *Centrosema pubescens*) are reared until fully grown and then cut back to a height of 60 cm. The plants are sprayed 7 days later with an aqueous emulsion of the test compound. The test plants are kept at 70% relative humidity and 600 lux artifical light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

Example B3: Growth regulation of soybeans

Soybeans of the "Hark" variety are sown in plastic containers in an earth/peat/sand mixture (6:3:1). The containers are put into a climatic chamber and the plants develop to the 5–6 trefoil leaf stage after about 5 weeks by optimum control of temperature, light, fertiliser addition, and watering. The plants are then sprayed with an aqueous mixture of a compound of formula I until thoroughly wetted. The concentration corresponds to up to 100 g a.i. per hectare. Evaluation is made about 5 weeks after application. Compared with untreated controls, the compounds of formula I markedly increase the number and weight of the harvested siliquae on the leading shoot.

Example B4: Growth inhibition of cereals

Summer barley (*Hordeum vulgare*) and summer rye (*Secale*) are sown in sterilised soil in plastic beakers in a greenhouse and watered as required. The cereal shoots are treated about 21 days after sowing with an aqueous spray mixture of a compound of the formula I. The concentration corresponds to up to 100 g of active ingredient per hectare. Evaluation of the growth of the cereals is made 21 days after application. A comparison with untreated controls shows that the growth of cereal plants treated with compounds of formula I is reduced (60–90% of the controls) and that the diameter of the stalks has in some cases increased.

Example B5: Growth inhibition of grasses

Seeds of the grasses *Lolium perenne*, *Poa pratensis*, *Festuca ovina*, *Dactylis glomerate* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of formula I. The concentration of test compound corresponds to a rate of application of up to 100 g a.i. per hectare. The growth of the grasses is evaluated 21 days after application. The compounds of formula I effect a reduction in new growth in the range of 10–30% in comparison with untreated controls.

What is claimed is:

1. A compound of the formula:

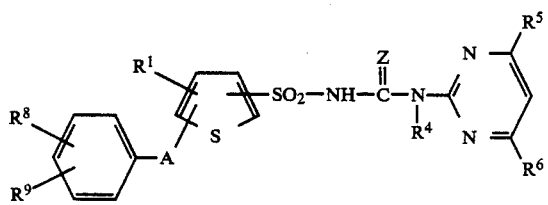

wherein:
- A is oxygen, sulfur, —SO—, —SO$_2$— or —(CR$^{10}$R$^{11}$)$_m$;
- R$^1$ is hydrogen, halo, nitro, C$_1$-C$_4$alkyl, C$_1$-C$_4$alkoxy, trifluoromethyl, trifluoromethoxy, difluoromethoxy, C$_1$-4alkylcarbonyl, or —COOR$^{14}$, in which R$^{14}$ is hydrogen, C$_1$-C$_4$alkyl, C$_2$-C$_4$alkenyl, C$_3$-C$_4$alkynyl, or C$_1$-C$_4$alkyl substituted with C$_1$-C$_4$alkoxy, halo, or phenyl;
- R$^4$ is hydrogen or C$_1$-C$_4$alkyl;
- each of R$^5$ and R$^6$, independently of the other, is hydrogen, halo, C$_1$-C$_4$alkyl, C$_1$-C$_4$alkoxy, C$_1$-C$_4$haloalkyl, C$_1$-C$_4$haloalkoxy, C$_1$-C$_4$alkylthio, C$_3$-C$_6$-dialkoxyalkyl, C$_1$-C$_4$haloalkylthio, C$_2$-C$_4$alkoxyalkyl, C$_3$-C$_6$cycloalkyl, or —NR$^{12}$R$^{13}$, in which each of R$^{12}$ and R$^{13}$, independently of the other, is hydrogen or C$_1$-C$_4$alkyl;
- R$^8$ is hydrogen, C$_1$-C$_4$alkyl, C$_1$-C$_4$alkoxy, halo, C$_1$-C$_4$haloalkyl, nitro, —COOR$^{14}$, C$_1$-C$_4$haloalkoxy, —OCR$^{15}$R$^{16}$COOR$^{14}$, or —OCR$^{15}$R$^{16}$CN, in which R$^{14}$ is as defined above and each of R$^{15}$ and R$^{16}$, independently of the other, is hydrogen or C$_1$-C$_4$alkyl; and
- R$^9$ is hydrogen, halo, C$_1$-C$_4$alkyl, C$_1$-C$_4$alkoxy, C$_2$-C$_4$alkoxyalkyl, or C$_2$-C$_4$alkoxyalkoxy;
- each of R$^{10}$ and R$^{11}$, independently of the other, is hydrogen or C$_1$-C$_4$alkyl;
- m is 0, 1, or 2; and
- Z is oxygen or sulfur;

and the agriculturally suitable salts thereof.

2. A compound according to claim 1, wherein Z is oxygen.

3. A compound according to claim 1, wherein R$^1$ is a hydrogen, Cl, F, CH$_3$, C$_2$H$_5$, CH$_3$O, CF$_3$ or CH$_3$CO.

4. A compound according to claim 1, wherein R$^5$ and R$^6$ together contain not more than 4 carbon atoms and R$^4$ is hydrogen.

5. A compound according to claim 1 which has the formula:

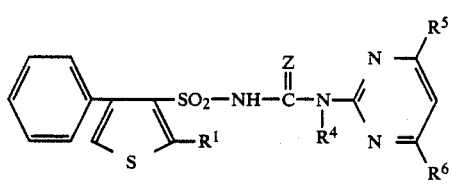

or

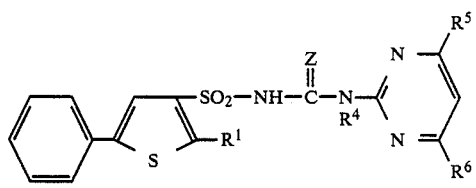

wherein R$^1$ is C$_1$-C$_4$alkoxycarbonyl.

6. A compound according to claim 1 which has the formula:

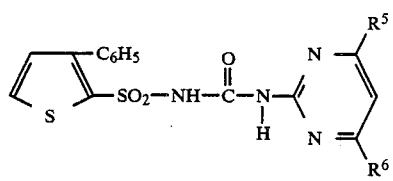

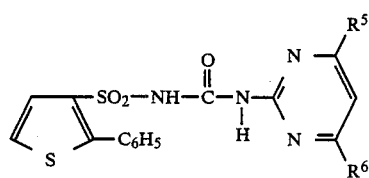

or

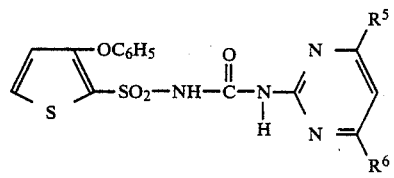

wherein and R$^5$ and R$^6$ together contain not more than 4 carbon atoms.

7. A compound according to claim 1 which has the formula:

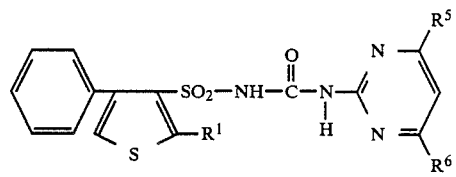

or

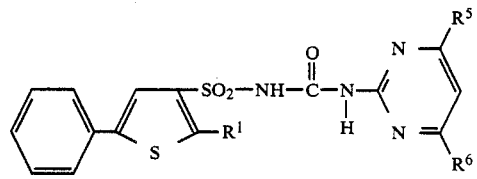

wherein R$^1$ is C$_1$-C$_4$alkoxycarbonyl and R$^5$ and R$^6$ together contain not more than 4 carbon atoms.

8. N-(2-Methoxycarbonyl-4-phenylthiophen-3-ylsulfonyl)-N'-(4-methoxy-6-methylpyrimidin-2-yl)urea according to claim 1.

9. A herbicidal and plant growth inhibiting composition which comprises as active ingredient, a substituted sulfonylurea of claim 1, together with a carrier and/or other adjuvants.

10. A method of controlling undesired plant growth, which method comprises applying to the plants or to the locus thereof an effective amount of a compound of claim 1, or of a composition containing such a compound.

11. A method of inhibiting plant growth, which method comprises applying to the plants or to the locus thereof an effective amount of a compound of claim 1, as active ingredient or of a composition containing such a compound.

12. A method of influencing plant growth for increasing yield, which method comprises applying to the plants or to the locus thereof an effective amount of a compound of claim 1, or of a composition containing such a compound.

13. A method according to claim 10 of selectively controlling weeds pre- or postemergence in crops of useful plants.

14. A method according to claim 11 of suppressing plant growth beyond the 2-leaf stage, which method comprises applying the active ingredient preemergence.

15. A method according to claim 3, wherein the crops are rice crops.

16. A compound of the formula:

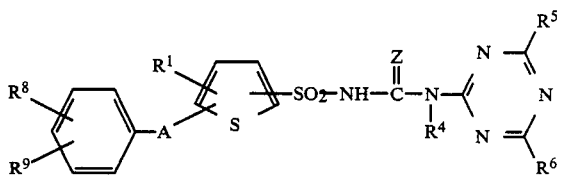

wherein:
A is oxygen, sulfur, —SO—, —SO$_2$— or —(CR$^{10}$R$^{11}$)$_m$;
R$^1$ is hydrogen, halo, nitro, C$_1$–C$_4$alkyl, C$_1$–C$_4$alkoxy, trifluoromethyl, trifluoromethoxy, difluoromethoxy, C$_1$–C$_4$alkylcarbonyl, or —COOR$^{14}$,
  in which R$^{14}$ is hydrogen, C$_1$–C$_4$alkyl, C$_2$–C$_4$alkenyl, C$_3$–C$_4$alkynyl, or C$_1$–C$_4$alkyl substituted with C$_1$–C$_4$alkoxy, halo, or phenyl;
R$^4$ is hydrogen or C$_1$–C$_4$alkyl;
each of R$^5$ and R$^6$, independently of the other, is hydrogen, halo, C$_1$–C$_4$alkyl, C$_1$–C$_4$alkoxy, C$_1$–C$_4$haloalkyl, C$_1$–C$_4$haloalkoxy, C$_1$–C$_4$alkylthio, C$_3$–C$_6$-dialkylamino, C$_1$–C$_4$haloalkylthio, C$_2$–C$_4$alkoxyalkyl, C$_3$–C$_6$cycloalkyl, or —NR$^{12}$R$^{13}$,
  in which each of R$^{12}$ and R$^{13}$, independently of the other, is hydrogen or C$_1$–C$_4$alkyl;
R$^8$ is hydrogen, C$_1$–C$_4$alkyl, C$_1$–C$_4$alkoxy, halo, C$_1$–C$_4$haloalkyl, nitro, —COOR$^{14}$, C$_1$–C$_4$haloalkoxy, —OCR$^{15}$R$^{16}$COOR$^{14}$, or —OCR$^{15}$R$^{16}$CN,
  in which R$^{14}$ is as defined above and each of R$^{15}$ and R$^{16}$, independently of the other, is hydrogen or C$_1$–C$_4$alkyl; and
R$^9$ is hydrogen, halo, C$_1$–C$_4$alkyl, C$_1$–C$_4$alkoxy, C$_2$–C$_4$alkoxyalkyl, or C$_2$–C$_4$alkoxyalkoxy;
each of R$^{10}$ and R$^{11}$, independently of the other, is hydrogen or C$_1$–C$_4$alkyl;
m is 0, 1, or 2; and
Z is oxygen or sulfur;
and the agriculturally suitable salts thereof.

17. A herbicidal and plant growth inhibiting composition which comprises as active ingredient a substituted sulfonylurea of claim 16, together with a carrier and/or other adjuvants.

* * * * *